United States Patent

Simmons et al.

[11] 4,009,713
[45] Mar. 1, 1977

[54] NEBULIZER

[75] Inventors: Raymond L. Simmons, San Jacinto; David E. Williams, Hemet; Edwin D. Hoyt, Hemet; Eugene B. Davis, Hemet, all of Calif.

[73] Assignee: Rama Corporation, San Jacinto, Calif.

[22] Filed: Apr. 23, 1976

[21] Appl. No.: 679,520

[52] U.S. Cl. .................... 128/193; 128/210; 261/DIG. 65; 219/273; 219/275; 239/138
[51] Int. Cl.² .................... A61M 16/00; B05B 1/24
[58] Field of Search .......... 128/192, 193, 194, 186, 128/188, 212; 261/DIG. 65, 142 R; 219/271, 272, 273, 275, 276; 239/136, 137, 138

[56] References Cited

UNITED STATES PATENTS

| 2,641,508 | 6/1953 | Stoner et al. | 219/273 |
| 3,588,057 | 6/1971 | Breiling | 128/188 |
| 3,695,516 | 10/1972 | Rogers | 239/135 |
| 3,836,079 | 9/1974 | Huston | 128/194 |

Primary Examiner—Robert W. Michell
Assistant Examiner—Henry J. Recla
Attorney, Agent, or Firm—Georges A. Maxwell

[57] ABSTRACT

A nebulizer for uniformly tempering and humidifying oxygen and different predetermined mixtures of oxygen-enriched air comprising a vessel containing a volume of water, oxygen supply means delivering oxygen into the vessel, air supply means conducting air into the vessel, and electric resistance heater means to heat the water in the vessel, said air supply and heater means including adjustable air metering means with a movable control part and said electric heater means including an adjustable control unit with a movable part, drive means connected with and between said movable parts whereby movement of one of said control parts results in predetermined corresponding movement of the other control part, whereby changes in the volume of air conducted into the vessel by said metering means results in predetermined corresponding heat output by the metering means and resulting tempering of the water.

15 Claims, 12 Drawing Figures

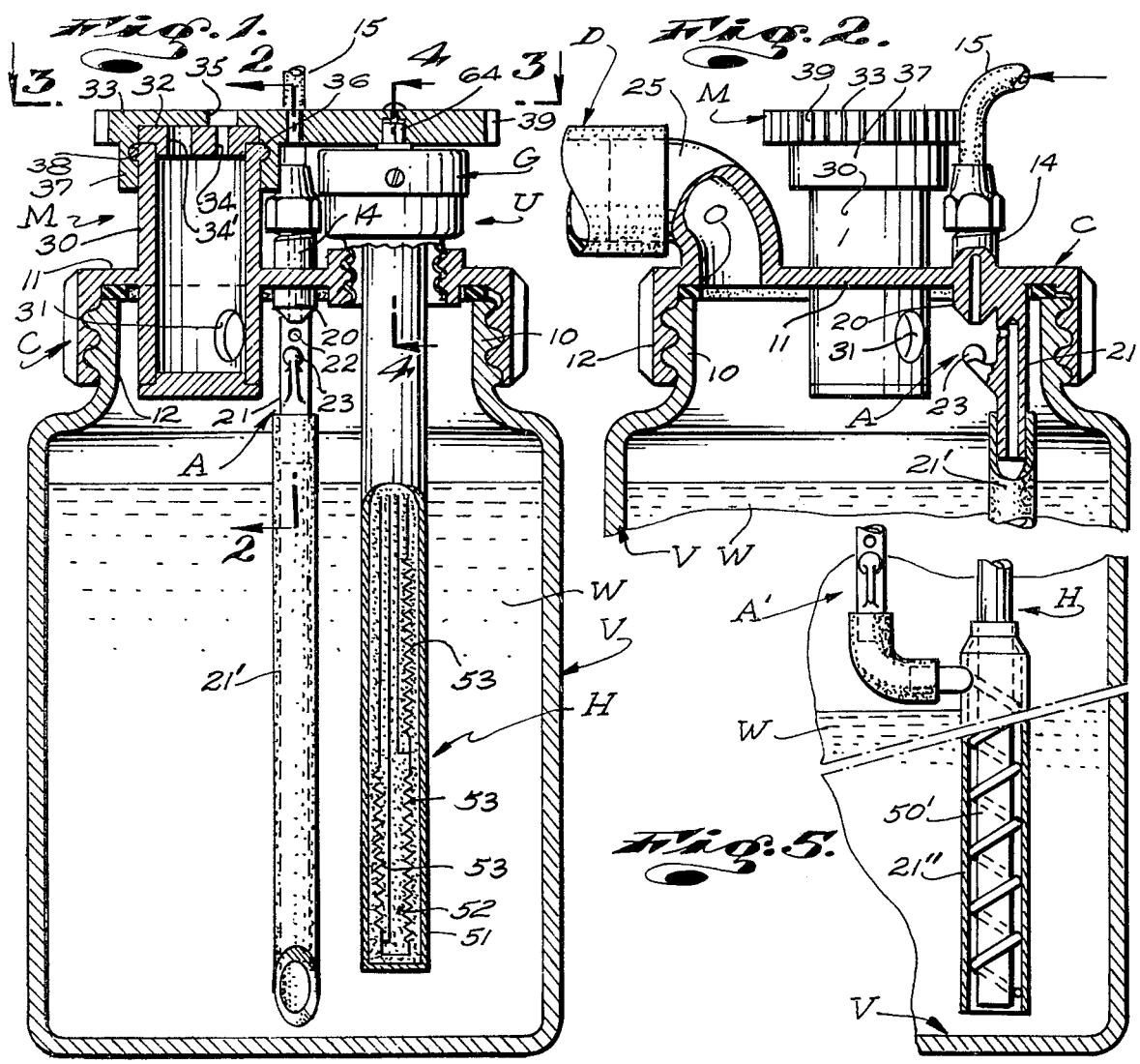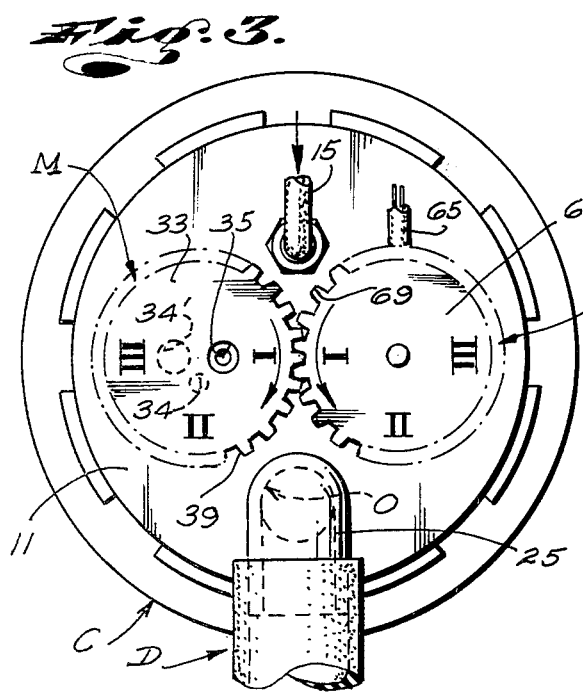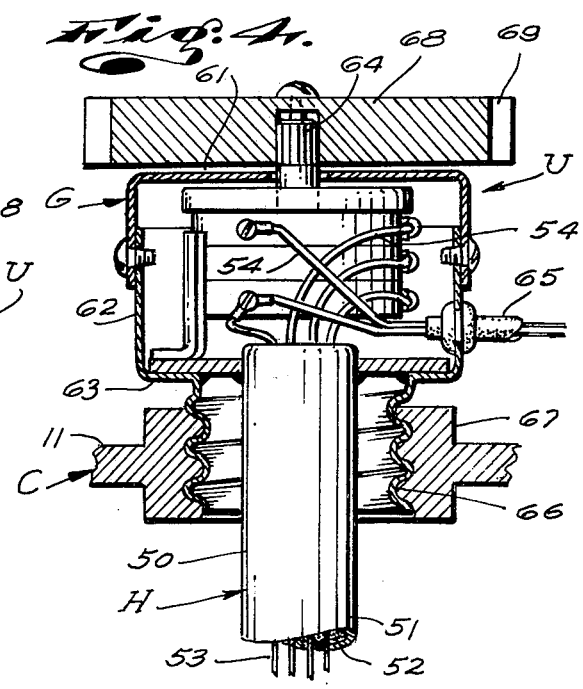

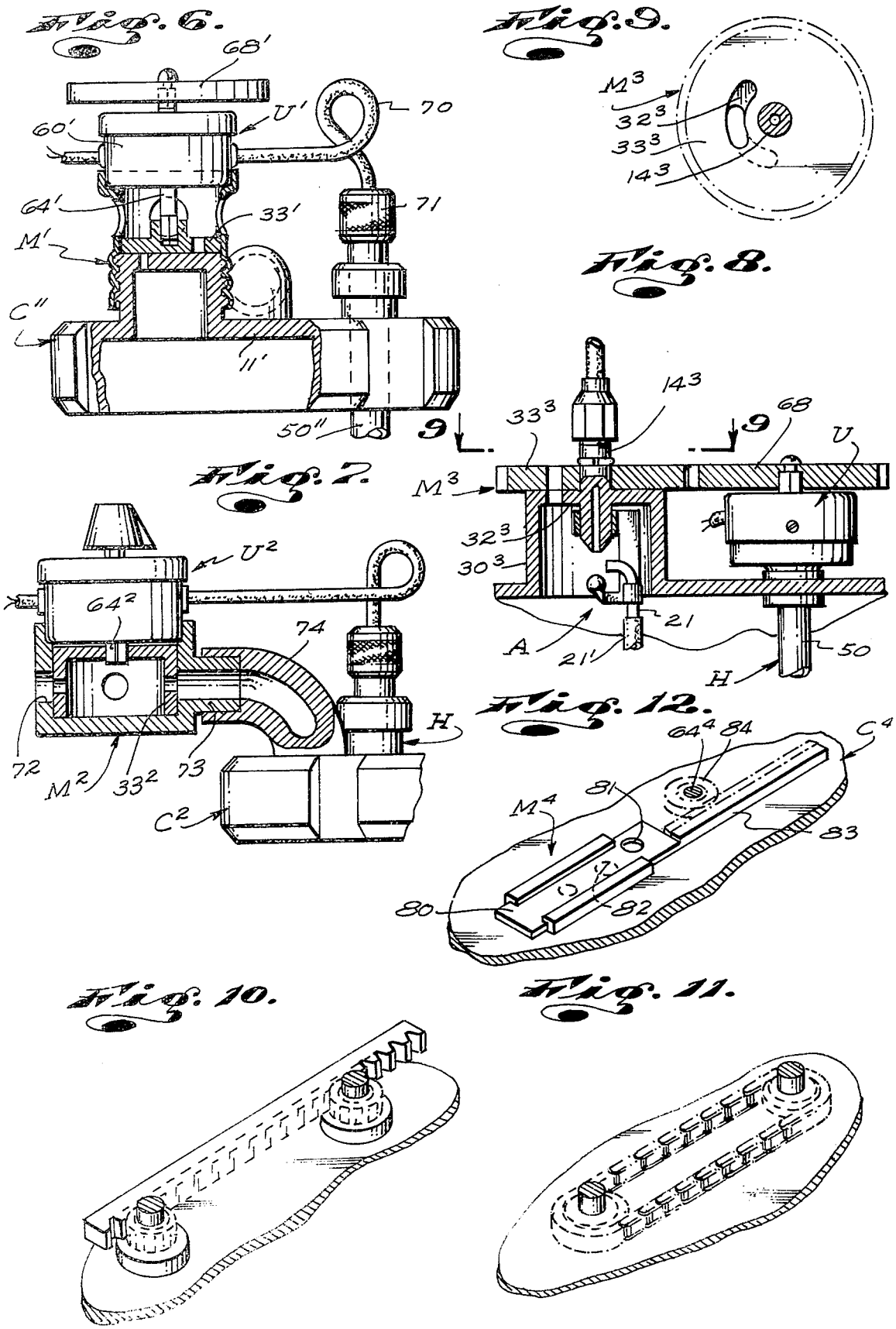

NEBULIZER

This invention has to do with a nebulizer and is particularly concerned with an improved nebulizer with interlocking adjustable air supply and heating means.

In the medical arts it is common practice to supply patients with oxygen or with oxygen-enriched air. Such supplying of patients with oxygen or oxygen-enriched air is accomplished by means of a supply of oxygen, under pressure, an oxygen supply line extending from the supply of oxygen to a mixer or blender which is operable to mix the oxygen with a predetermined volume of air, when desired, whereby oxygen or a desired mixture of oxygen-enriched air is attained and a delivery line or hose extending from the blender to the patient and conducting the oxygen or oxygen-enriched air to the patient for consumption or use. In practice, a mask or tent is provided at a remote or free end of the hose to effect transfer of the oxygen or oxygen-enriched air to the patient's respiratory system. Further, in practice, a suitable flow control valve or metering device is provided to control the flow of oxygen to the blender and the blender is provided or incorporates adjustable air metering or flow control means to control the flow of air into the nebulizer, whereby a desired mixture composed or predetermined volumes of air and oxygen can be effectively established and maintained, as desired or as circumstances require.

In addition to the proportional mixing and/or blending of air and oxygen, as noted above, it has been found desirable and oftentimes imperative that the temperature and/or the humidity of the oxygen or oxygen-enriched air to be delivered to patients be carefully and accurately controlled in order to avoid discomfort and possible irreparable harm to the patient.

In practice it is most desirable that the temperature of the oxygen or oxygen-enriched air delivered to patients be at or as near as possible to body temperature (98.6° F.) so that the patients are subjected to as little thermal shock as possible. Further, in practice, it is generally most desirable that the oxygen or oxygen-enriched air delivered to patients be humidified to near saturation with water, whereby the oxygen or oxygen-enriched air does not tend to dry and parch the patient's respiratory system and cause them discomfort, troubled swallowing and the like. The attaining of such desired ends is considered imperative to assure the patients a maximum of labor-free and comfortable rest.

As a result of the above, it has become common practice to humidify and to heat the oxygen or oxygen-enriched air by means of what is commonly referred to in the art as a nebulizer. Nebulizers of the class here concerned with generally comprise a container or vessel in which a supply of water is maintained and an electric heater means to temper the water.

Such nebulizers commonly include suitable means for working on the air, oxygen and/or tempered water, whereby the oxygen or oxygen-enriched air is effectively humidified and tempered.

In practice, where nebulizers of the class here concerned with are provided, they incorporate the aforementioned air and oxygen blending means, which blending means, as noted above, include suitable air metering or flow control means.

Further, in practice, where such nebulizers are provided, the heater means provided to heat the water are adjustable, whereby the temperature of the water can be adjusted in an effort to attain an acceptable balance between the temperatures of the water, air and oxygen flowing through the structures, whereby satisfactory tempering of the humidified oxygen or oxygen-enriched air is established and maintained.

While adjustable, multi-output or variable output heaters have been used in this art, to the best of our knowledge and belief, the established output of such heaters has been arrived at arbitrarily and without reference to the specific volumes of material to be heated. At best, heater output has been approximated to meet demands for heat within rather wide and ill-defined ranges.

Heating of the water also has a direct effect in humidifying the oxygen or oxygen-enriched air. Accordingly, controlled heating of the water is not solely for the purpose of tempering the materials In practice, the oxygen supply is most often in the form of portable cylinders of compressed oxygen, while in other instances it is in the form of a piping system in and throughout a facility (such as a hospital) and which serves to deliver oxygen to desired stations or locations throughout the system at fixed, constant pressure.

As a result of the above, and in view of other circumstances, oxygen support systems of the character here concerned with and with nebulizers included therein are designed to operate at a set predetermined pressure which is compatible with the majority of different oxygen supplies that might be encountered.

As a general rule, suitable pressure regulating means or devices are provided with and considered a part of most oxygen supply means and/or systems in the medical arts.

In accordance with the above, and with oxygen supply systems or means and with nebulizers of the character referred to above; in the course of establishing a properly humidified and tempered supply of oxygen or oxygen-enriched air for a patient, the doctor, nurse or technician need only work those means provided for controlling the supply of air and those means provided to adjust the output of the heater means of the nebulizers.

As a general rule, when oxygen alone is delivered by an oxygen support system of the character referred to above, the volume of gases to be heated is at a minimum and the output demand of the heater means, to effect proper tempering of the oxygen is at a minimum. When air is added to the supply of oxygen and the volume of gas to be tempered is increased, the output demand on the heater means is increased. As a result of the above, as the supply of air in such systems is increased, the output of the heater means must be increased substantially proportionately therewith.

Accordingly, each time a person adjusts the air supply in such systems, he must make appropriate corresponding adjustment of the heating means.

While the above noted procedure of adjustment appears or seems to be simple, it has been found that it is not infrequent that persons in charge of such systems or apparatus will make one adjustment and forget the other required adjustment or will inadvertently make counter adjustments, that is, increase the air supply or the heater output when it should have been decreased. Such errors can produce fatal results in some instances.

Since the outputs or ordinary multi-output heaters used in this art are arrived at arbitrarily and are unrelated to specific volumes of water and gas to be heated, adjustment of the heating means seldom results in proper tempering of the water and gases and most often results in what can best be described as an approximate adjustment within excessive tolerances.

An object and feature of our invention is to provide an improved nebulizer of the general type or class referred to above wherein the air control means and control for the heater means are interlocked and such that an adjustment of either of said means works to properly adjust the other of said means, whereby reltive maladjustment of the two related controls is made impossible and whereby those adverse effects which are likely to result from maladjustment of those means is avoided.

It is an object and feature of our invention to provide a structure of the character referred to wherein the oxygen supply and air control means are operable and/or adjustable to effect delivery of selectable, predetermined volumes of gas and wherein the heater is designed and constructed to have outputs related to and balanced with the several volumes of gas whereby proper, desired, tempering of the gases is assured.

It is an object and feature of our invention to provide a nebulizer structure of the general character referred to wherein the air control means includes a movable control part and wherein the control for the heater means includes a movable control part and a structure wherein the movable control parts are drivingly coupled together, whereby movement of one results in corresponding moving of the other.

It is another object of our invention to provide a structure of the general character referred to above wherein either or both of said movable parts can be manually moved to effect desired adjustment of the structure.

Yet another object and feature of our invention is to provide a structure of the general character referred to which is simple, durable and practical in both structure and in operation; a structure which meets all existing requirements as regards health and safety in those environments in which it is intended and likely to be used and a structure which is easy, simple and foolproof in operation.

The foregoing and other objects and features of our invention will be apparent and will be fully understood from the following detailed description of typical preferred forms and applications of our invention, throughout which description reference is made to the accompanying drawings, in which:

FIG. 1 is a sectional view of a nebulizer embodying our invention;

FIG. 2 is a sectional view taken as indicated by line 2—2 on FIG. 1;

FIG. 3 is a sectional view taken substantially as indicated by line 3—3 on FIG. 1;

FIG. 4 is a sectional view taken substantially as indicated by line 4—4 on FIG. 1;

FIG. 5 is a sectional view of a portion of a nebulizer showing another form or embodiment of our invention;

FIG 6. is a sectional view of a portion of a nebulizer showing another form or embodiment of our invention;

FIG. 7 is a sectional view of a portion of a nebulizer showing another form or embodiment of our invention;

FIG. 8 is a sectional view of a portion of a nebulizer showing another form or embodiment of our invention; and FIGS. 9, 10, 11 and 12 are diagrammatic views of other drive means that can be advantageously embodied in carrying out our invention.

In FIGS. 1 through 4 of the drawings we have illustrated one form of nebulizer embodying our invention, which nebulizer is shown as including a jar-like container or vessel V with an upwardly opening externally threaded neck 10 and carrying a supply of water W; a closure or cap C with a flat top wall 11 and an internally threaded annular skirt 12 threaded on the neck and closing the vessel V; a gas conducting nipple 14 carried by and projecting upwardly from the wall 11 of the cap C and suitably connected with an oxygen supply line 15 extending from a suitable high-pressure, pressure regulated source or supply of oxygen (not shown).

The nebulizer next includes air supply means M carried by the cap C and adapted to conduct air into the vessel and includes mixing means in the vessel to commingle water, oxygen and air in the vessel to effect heat transfer therebetween and humidifying of the gases. The mixing means, in the preferred form of the invention, is in the nature and/or form of an atomizer or aspirator means A carried by and depending from a top wall of the cap into the vessel V, above the water W therein. The means A includes a nozzle 20 communicating with the nipple 14 and directs a high velocity jet of oxygen into the interior of the vessel below the cap and above the water. The means A next includes an elongate suction tube 21 adjacent the nozzle and the gas jet issuing therefrom and depending into the water, and a low pressure outlet port 22 in the tube in close proximity to the outlet of the nozzle and in the low pressure zone created by the jet of gas issuing from the nozzle.

Finally, the aspirator includes a diffuser 23 arranged in the path of the jet, in spaced relationship from the nozzle and downstream of the port 22. The jet of oxygen creates a low pressure zone in the interior of the vessel adjacent the port 22. The low pressure thus established draws water through the tube 21 and the port 22. The water flowing from the port 22 combines with the jet of oxygen. The jet of oxygen and the water carried thereby impinges upon the diffuser, breaking up, diffusing and/or atomizing the water and causing the water to scrub the oxygen so as to saturate the oxygen with water.

In practice, and as shown, the tube 21 can be sectional and can comprise an upper section formed integrally with the aspirator A and a removable extension 21' which extends down into the vessel and the water W therein.

In practice, the mixing means can be in the form of a scrubber comprising a horizontally disposed perforated bubble plate submerged in the water in the vewsel and having ducts related to it for conducting air and/or oxygen to the lower side thereof for distribution in and throughout the water.

The nebulizer next includes a discharge opening O in the cap C to conduct humidified oxygen or oxygen-enriched air from within the upper portion of the vessel and which connects with a delivery hose D to deliver the oxygen or oxygen-enriched air to a patient (not shown). In the case illustrated, the cap C is provided with an upwardly and radially outwardly extending gooseneck type hose coupling 25 communicating with the opening O and engaged with the delivery hose D, as clearly illustrated in FIGS. 2 and 3 of the drawings.

The above referred to air supply and metering means M is operable from a closed position to opened positions which permit metered volumes of air to be drawn into the vessel V by the minimum pressure generated therein by the jet of oxygen delivered into the vessel by the nozzle 20 of the aspirator means A. The means M can vary widely in form and is shown as including an elongate vertical air conducting duct 30 extending through and carried by the top wall 11 of the cap C. The duct 30 has a lower portion which extends into the low pressure zone in the upper portion of the vessel, an air transfer opening 31 communicating with the interior of the vessel V and the interior of the duct, an apertured top wall or plug 32 closing the upper end of the duct and a valving plate 33 shiftably carried by the plug and/or duct. The plug 32 has a plurality of spaced apertures 34 and 34' of different diameter and volumetric flow capacity while the plate has a single valving port 35 equal or greater in diameter and capacity than the largest of the apertures and which is selectively shiftable into register with one or the other of the apertures by moving the plate relative to the plug. The port 35 is also positionable out of register with either of the apertures to effectively shut off the supply of air.

In the case illustrated, the plug 32 is a round disc-like part with a cylindrical side wall and with a flat top. The plug is suitably engaged and fixed in the upper end of the duct. The upper end of the duct is provided with an outwardly projecting annular bead 36. The apertures 34 and 34' extend axially, vertically through the plug and are arranged in predetermined radial and circumferential spaced relationship therein to open at the top of the plug and to communicate with the interior of the duct.

The valving plate is shown as a flat disc which is concentric with the plug and has a flat bottom surface in sliding supported engagement with the top of the plug. The valving port in the disc is a vertical through opening and is arranged with its axis spaced radially from the axes of the plug and plate the same distance that the axes of the apertures are spaced from the axes of the plug and plate. The plate is larger than the plug in diametric extent to project radially therefrom and is provided with an annular skirt 37 which depends therefrom and into sliding engagement about the exterior of the upper portion of the duct. The skirt is provided with an annular radially inwardly opening groove 38 in which the bead 36 on the duct is slidably engaged, whereby the plate is retained on and about the duct and the plug for substantial free rotation relative thereto.

Finally, the exterior of outer periphery of the plate is formed or provided with gear teeth 39. The teeth 39 are simple, spur-gear teeth and can be of any desired or suitable size and shape which render the plate attractive and convenient for manual engagement. The purpose and function of the gear teeth 39 will be described in the following.

If desired, the valve plate 33 can be properly referred to as a gear-valve-plate. Further, while the gear teeth are shown formed integrally on the plate, about the periphery thereof, it will be apparent that they could be formed on a separate ring, or sleeve-like part suitably related to the plate, without departing from the spirit of our invention. Accordingly, the gear structure, per se, can be considered separate from the plate and can be defined as a gear on or related to the plate or the movable or rotatable part of the metering means M.

With the means M set forth above, and the considering that the flow of oxygen into and through the structure is at a substantial steady and constant pressure and rate, it will be apparent that accurate metering and conducting of predetermined volumes of air into and through the structure, by the means M herein provided, can be effected. In practice, and in accordance with common requirements and in the medical art, the means M is established so that the flow of metered volumes of air can be selectively established in and through the nebulizers, whereby oxygen-enriched air comprising, for example, 40 percent or 80 percent oxygen can be effectively established for delivery to a patient. It is to be noted that when air is drawn through the means M into the vessel V and to the low pressure zone established by the aspirator A, the air is scrubbed with the atomized or diffused water and, like the oxygen, is humidified or saturated with water.

The nebulizer next and finally includes the heater means H which serves to heat the water W in the vessel and to thereby temper the humidified oxygen and/or air which flows out of the opening O and is delivered to the patient. The heater means H that we provide in the nebulizer structure comprises an elongate vertical cartridge heater 50 with an upper service end and a lower free end. The heater 50 comprises an outer tubular metal sheath 51 suitably closed and sealed at its opposite end, a filler 52 of magnesium oxide or other dielectric insulating material and an electric resistance heating element or elements 53 arranged within and carried by the filler. The element or elements 53 extend longitudinally of the heater and have power leads 54 extending longitudinally outward through and from the upper service end of the sheath. The heater 50 is a variable output heater structure and is under control of a suitable control unit or device U.

In practice, the heater can be provided with a single resistance element 53 and the unit U can be a resistive or transistorized current limiting or modifying device which serves to effectively vary or modify the current flowing to the elements of the heater and to thereby change or adjust the heat output of the heater.

In the preferred carrying out of the invention and in light of weight, cost, size and dependability factors, the unit U is a multiple position rotary switch and the heater 50 is provided with a plurality of resistance elements 53. As shown in the drawings, the heater has three elements 53 and the unit U or switch is a three position rotary switch and is connected with the leads 54 of the heater, whereby one, two or three of the elements 53 can be selectively energized, whereby the heater 50 is capable of producing three different, predetermined heat outputs to meet three output demands.

The three outputs of the heater are established and directly related to the three different predetermined, designed, outputs of oxygen and oxygen-enriched air to be selectively produced and delivered by the nebulizer and is such that the water W in the nebulizer is heated to that extent which is necessary and desired to properly temper selected oxygen or oxygen-enriched air mixtures established and discharged by the nebulizer for delivery to and/or by a patient.

It is to be understood and it will be apparent that in practice, if the number of different outputs of oxygen and oxygen-enriched air mixtures is changed or increased, the number of different outputs afforded by the heater means H is increased accordingly and the heater outputs are appropriately balanced with their related gas mixtures.

In practice, desired balancing of the heater outputs and gas mixtures could be accomplished by altering the gas mixtures so as to balance with predetermined heater outputs. Such a procedure, however, is believed to be less acceptable in the medical arts since physicians are accustomed to prescribing fixed mixtures of gas for the patients, and would be reluctant to accept different and unusual mixtures dictated by a machine.

The switch or unit U and the heater 50 can be separate, distinct units suitably connected by means of a power cable.

In the form of the invention now under consideration, the heater 50 and unit U are integrated into a single heating means H releasably engaged with and carried by the cap C.

The unit U is provided with a cannister or case G with a top wall structure 61, a cylindrical side wall 62 and a bottom wall structure 63. The rotary switch unit is suitably mounted in the case and has a vertical, rotatable operating stem 64 projecting upwardly therefrom and through an opening in the top wall structure 61. The upper end of the heater 50 is engaged through and fixed in an opening in the bottom wall structure. The leads 54 extending from the heater and connected with the switch are housed within the case, substantially as shown.

The side wall 62 of the case has an opening through which a power supply or service cord 65 for the heater means extends.

The unit U or the case 60 thereof next includes a threaded annular reduced skirt 66, depending from the side wall about the upper end portion of the heater, which skirt is normally threadedly engaged in an elongate vertical internally threaded collar or support sleeve 67 formed integrally in the top wall 11 of the cap C, as clearly illustrated in FIGS. 1 and 4 of the drawings.

Finally, the heater means H that we provide includes a manually engageable gear wheel or operating disc 68 secured to the upper end of the upper shaft 64 to occur in fixed spaced relationship above the case and having gear teeth 69 about its perimeter. The gear teeth 69 are formed to be complimentary with and are engageable with the teeth 39 on the disc 33 of the means M (see FIG. 3 of the drawings).

The heater 50 extends downwardly from the cap C, through the vessel V and into the water W, as shown in FIG. 1 of the drawings.

The apertures 34 and 34' in the plug 32 of the means M are spaced circumferentially through an arc of rotation which is equal to the arc of rotation of the switch when the switch is operated from one position to another. The vertical axes of the means M and H are parallel and spaced from and about the vertical axis of the cap C so as not to interfere with the means for delivering oxygen to the nebulizer or with the means for delivering oxygen or oxygen-enriched air from the nebulizer and which are related to the cap C. The means M and H are established to locate the discs 33 and 68 on a common horizontal plane spaced above the top of the cap where they are clear of other structure and means and are readily manually accessible. the discs 33 and 68 are equal in diameter and are of such diametric extent that their gear teeth establish driving engagement with each other, as clearly shown in FIG. 3 of the drawings.

In the event the unit U is a rheostat type unit with infinite positioning characteristics, the diameters of the wheel 33 and disc 68 can be different and varied so as to effect an increase or decrease of rotation of one relative to the other and so that rotation of one effects a desired, proportional rotation of the other.

In practice, the wheel 33 and the disc 68 can be provided with three circumferentially spaced markings, numbers or calibrations on the top visible sides or surfaces thereof which markings are arranged to be aligned and/or to register with each other when the means M and H are in each of their three selectible positions.

With the structure set forth above, it will be apparent that when oxygen or a selected oxygen-enriched air mixture is established in and by the nebulizer, it is properly and effectively humidified and tempered. It will be further apparent that when it is desired to change the output of the nebulizer, that is, to change its output from straight oxygen or one of the two mixtures of oxygen-enriched air, or vice-versa, and one disc 33 or 68 of the means M and H is manually engaged and rotated to effect that change, the other disc is rotated therewith and to the same, or to a different but corresponding, extent, whereby synchronous related adjustment of both the means M and H from one position to another is assured and error in adjustment is avoided.

In FIG. 5 of the drawings, we show a portion of our invention in another or modified form. In this modified form of our invention the suction tube of the means A' has a section 21" engaged about the lower portion of the heater 50', whereby only that water which is drawn through the tube section 21" is heated. In such a modified form of the invention, the output and/or power demand made upon the heater 50' can be materially reduced. Further, since the entire volume of water in the vessel V not be heated, heating of the water delivered to the means A' is not effected by differences in the volume of water in the vessel.

In practice, the tube section 21" is maintained in spaced relationship from the heater 50' by a helical spacer in the annulus between the tube and the heater. The spacer also serves to direct water flowing in the annulus about the heater for uniform heat transfer therebeween.

In FIG. 6 of the drawings we show another form of our invention wherein the heater 50" and control unit U' therefor are separate. In this form of the invention, the unit U' is arranged in axial alignment and above the means M' and the shaft 64' of the switch has a lower driving end engaged with the valving disc 33' of the means M'. In this form of the invention, the case 60' is threaded on and about the upper end of the duct 30' and the disc 68' of the unit U' is the single, required, manually operable control part of the construction.

In this form of the invention, the switch of the control unit U has a coupling cable 70 which extends to and is connected with the upper end of the heater 50" by means of a suitable electrical disconnect plug 71. Also, in the form of the invention now under consideration the duct 30' is modified. The duct 30' simply terminates and opens at the bottom surfce of the top wall 11' of the cap C".

Since other details of this modified form of our invention can vary widely in form without departing from the spirit of our invention, detailed description thereof will not be entered into.

In FIG. 7 of the drawings, we disclose yet another form of our invention wherein the means $M^2$ is separate from the cap $C^2$ and comprises a tubular body $30^2$ and an apertured rotary sleeve valve member $33^2$ in the body $30^2$. The body has an air inlet opening 72 at one side and an air outlet fitting 73 at its other side. The sleeve 33² is rotated in the body to selectively move the metering apertures therein into and out of register with the opening 72 and fitting 73. The fitting 73 connects with a gooseneck like air fitting 74 on the cap C².

In this form of our invention the control unit U² is essentially the same as the unit U' in the form of the invention shown in FIG. 6 and is such that its shaft 64² engages and drives the valving member or sleeve 33² as is required.

In FIG. 8 of the drawings, we have shown still another form of our invention wherein the means A³ and the means M³ are combined or directly and structurally interrelated. In this form of our invention, the aspirator means A³ is arranged within the chamber defined by the downwardly opening duct 30³ and below the apertured plug 32³ of the means M³. The nipple 14³ to connect the oxygen supply projects freely upwardly through the plug and valving member or disc 33³.

The disc 33³ can be related to the disc 68³ of a heater means H³ which is similar to the means H in the first form of the invention and in the same manner that the means M is related to the means H in the first from of the invention.

Further, in the last form of the invention and as clearly shown in FIG. 9 of the drawings, the plug 32³ and disc 33³ are provided with registerable, elongate arcuate apertured which serve or attain the same and results as do the pluralities of registerable apertures in the other forms of the invention. The pair of elongate apertures are the equivalent of the pluralities of apertures.

Since other details of the last noted form of our invention can vary widely in form and construction without departing from the spirit of our invention, further detailed consideration thereof can and will be dispensed with.

In practice, where the operating axes of the metering means M and control means for the heater means H are on laterally spaced parallel axes and the utilization of meshed gear members, such as are provided in the first form of the invention, is not desirable, a single rack and beveled gear drive means, such as is diagrammatically shown in FIG. 10 of the drawings, or a chain and sprocket drive means, such as diagrammatically shown in FIG. 11 of the drawings, can be employed, if desired or as circumstances require.

In FIG. 12 of the drawings, the metering means M⁴ comprises an elongate, axially shiftable valving plate 80 with an air conducting aperture 81 and slidably engaging the top of the cap C⁴ in alignment with and overlying a series of apertures 82. The plate is fixed to a rack 83 engaged by a gear 84 on the operating shaft 64⁴ for a related heater control unit (not shown). In this form of the invention, the drive is lineal to rotary or vice versa, rather than rotary as in the other preceding forms of the invention.

It is to be particularly noted that the air metering means in this form of the invention is essentially the same as in the other forms of the invention with the exception that the ported parts are shifted or moved lineally rather than rotationally relative to each other.

It will be readily apparent from the foregoing descriptions of the preferred and several modified forms of our invention that the primary object and feature of the invention is to provide a nebulizer of the general type or class herein concerned with having adjustable air metering and adjustable heater means which are drivingly coupled to each other, whereby each of said means is automatically adjusted with the other of said means when either of said means is sought to be adjusted.

It will be further apparent from the preceding that the obtaining of such end results can be attained in various ways by various means or structure without departing from the spirit of our invention.

Having described only typical preferred forms and applications of our invention, we do not wish to be limited to the specific details herein set forth, but wish to reserve to ourselves any modifications and/or variations that may appear to those skilled in the art and which fall within the scope of the following claims.

Having described our invention, we claim:

1. A nebulizer comprising a closed vessel, a supply of water in the vessel, oxygen supply means connected with a source of oxygen under pressure and delivering oxygen into the vessel, a resistance heater related to the vessel to heat the water in the vessel, control means controlling the heat output of the heater and positioned at the exterior of the vessel, air supply means communicating with the interior of the vessel and including air metering means controlling the flow of air into the vessel, mixing means within the vessel to commingle water, air and oxygen within the vessel and to effect tempering and humidifying the air and oxygen, delivery means conducting oxygen and oxygen-enriched air mixtures from the vessel, said control means for the heater and for the air metering means having movable control parts and drive means connected with and between said parts and establishing driving engagement therebetween whereby both of said parts are moved and their related means are adjusted when one of said parts is moved to adjust its related means.

2. The nebulizer set forth in claim 1 wherein said parts are rotary parts, one of said parts having a manually engageable drive member to rotate that part and said drive means transmitting rotary driving force from said one part to the other.

3. The nebulizer set forth in claim 2 wherein said parts are in axial alignment and said drive means includes a torsional drive coupling between said parts.

4. The nebulizer set forth in claim 3 wherein said drive means includes gears on said parts and a rack engaged with and extending between the gears.

5. The nebulizer set forth in claim 2 wherein the axes of said rotary parts are parallel and spaced apart laterally.

6. The nebulizer set forth in claim 5 wherein said drive means include gear wheels on said parts and said gear wheels are in meshed driving engagement with each other.

7. The nebulizer set forth in claim 5 wherein said drive means includes sprockets on said parts and a drive chain engaged about and extending between the sprockets.

8. The nebulizer set forth in claim 1 wherein said metering means comprises a fixed part relative to which said movable part of the metering means moves, said relatively movable parts having air conducting apertures movable into and out of communication and register with each other when the relatively movable parts are moved relative to each other.

9. The nebulizer set forth in claim 8 wherein the control means for the heater is a multiposition swtich controlled by movement of the movable part of said control means therefor, whereby the heater can be selectively adjusted for predetermined different heat outputs, said drive means moving the movable part of the metering means to establish different predetermined volumetric flows of air into the vessel when the switch is in each of its positions.

10. The nebulizer set forth in claim 1 wherein said mixing means includes an aspirator in the vessel above the water having a high pressure nozzle connected with the source of oxygen under pressure and directing a high velocity jet of oxygen into the vessel, a low pressure port in communication with a low pressure zone in the vessel established by the jet, a suction tube extending from the port into the water and through which water is drawn to combine with the jet by the low pressure zone.

11. The nebulizer set forth in claim 10 wherein said aspirator includes a diffuser spaced from said nozzle and said port in axial alignment with the jet and upon which the jet and water carried by the jet impinge.

12. The nebulizer set forth in claim 1 wherein said vessel includes an elongate vertical fluid container with an upwardly opening threaded mouth at its upper end and a cap threaded with and overlying the mouth, said mixing means, heater means, air supply means and delivery means are secured with and carried by the cap.

13. The nebulizer set forth in claim 12 wherein the cap has a vertical flow tube with an open lower end, said metering means is at the upper end of said flow tube and said mixing means is positioned within said flow tube below the metering means.

14. The nebulizer set forth in claim 1 wherein one of said control parts is a rotary movable part and the other of said control parts is movable lineally.

15. The nebulizer set forth in claim 14 wherein said drive means includes a gear on the rotary movable part and a rack on the lineally movable part and engaged with said gear.

* * * * *